US007718170B2

(12) United States Patent
Kiss

(10) Patent No.: US 7,718,170 B2
(45) Date of Patent: May 18, 2010

(54) ALKALINE PHOSPHATASE COMPOSITIONS TO REDUCE SKIN CANCER

(75) Inventor: Zoltan Kiss, Austin, MN (US)

(73) Assignee: Essential Skincare, LLC, Austin, MN (US)

( * ) Notice: Subject to any disclaimer, the term of this patent is extended or adjusted under 35 U.S.C. 154(b) by 258 days.

(21) Appl. No.: 11/465,876

(22) Filed: Aug. 21, 2006

(65) Prior Publication Data

US 2008/0044397 A1 Feb. 21, 2008

(51) Int. Cl.
*A61K 38/46* (2006.01)
(52) U.S. Cl. ..................... 424/94.6; 424/94.1
(58) Field of Classification Search ................. None
See application file for complete search history.

(56) References Cited

U.S. PATENT DOCUMENTS

| | | | |
|---|---|---|---|
| 4,347,841 A | 9/1982 | Benyó | |
| 4,818,540 A | 4/1989 | Chien et al. | |
| 5,461,030 A | 10/1995 | Lindenbaum | |
| 5,556,645 A | 9/1996 | Bockman et al. | |
| 5,591,709 A | 1/1997 | Lindenbaum | |
| 7,312,198 B2 * | 12/2007 | Kiss | 514/12 |
| 7,374,754 B2 * | 5/2008 | Kiss | 424/94.1 |
| 2005/0048046 A1 | 3/2005 | Kiss | |
| 2007/0148155 A1 * | 6/2007 | Kiss | 424/94.6 |
| 2008/0075707 A1 * | 3/2008 | Kiss | 424/94.6 |

OTHER PUBLICATIONS

Martinez et al., (2001), "The management of melanoma and nonmelanoma skin cancer: A review for the primary care physician," Mayo Clin. Proc. 76, 1253-1265.
Atkins et al., (2006), "Innovations and challenges in melanoma: Summary statement from the first Cambridge conference," Clin. Cancer Res. 12 (7 Suppl), 2291s-2296s.
Atkins, (2006), "Cytokine-based therapy and biochemotherapy for advanced melanoma," Clin. Cancer Res. 12 (7 Suppl), 2353s-2358s.
Elaraj et al., (2006), "The role of interleukin 1 in growth and metastases of human cancer xenografts," Clin. Cancer Res. 12, 1088-1096.
Varfolomeev et al., (2004), "Tumor necrosis factor: an apoptosis juNKie?," Cell 116, 491-497.
Bennloch et al., (2006), "Bcl-2 and Mn-SOD antisense oligodeoxynucleotides and glutamine-enriched diet facilitate elimination of highly resistant B16 melanoma cells by tumor necrosis factor-$\alpha$ and chemotherapy," J. Biol. Chem. 281, 69-79.
Bedogni et al., (2004), "Topical treatment with inhibitors of the phosphatidylinositol 3'-kinase/Akt and Raf/mitogen-activated protein kinase kinase/extracellular signal-regulated kinase pathways reduces melanoma development in severe combined immunodeficient mice," Cancer Res. 64, 2552-2560.
She et al., (2000), "Growth factor-like effects of placental alkaline phosphatase in human fetus and mouse embryo fibroblasts," FEBS Letters, 468, 163-167.
She et al., (2000), "Placental alkaline phosphatase, insulin, and adenine nucleotides or adenosine synergistically promote long-term survival of serum-starved mouse embryo and human fetus fibroblasts," Cellular Signalling 12, 659-665.
"Use of Placental Alkaline Phosphatase to Promote Skin Cell Proliferation," U.S. Appl. No. 10/653,622, filed Sep. 2, 2003.
Kozlenkov et al.,(2002), "Function assignment to conserved residues in mammalian alkaline phosphatase," J. Biol. Chem. 277, 22992-22999.
Beck et al., (1994), "Expression of human placental alkaline phosphatase in *Escherichia coli*," Protein Expression and Purification 5, 192-197.
Heimo et al., (1998), "Human placenta alkaline phosphatase: Expression in Pichia pastoris, purification and characterization of the enzyme," Protein Expression and Purification 12, 85-92.
Baldi et al., (2005), "Ferritin contributes to melanoma progression by modulating cell growth and sensitivity to oxidative stress," Clin. Cancer Res. 11, 3175-3183.
Carlevaro et al., (1997), "Transferrin promotes endothelial cell migration and invasion: Implication in cartilage neovascularization," J. Cell. Biol. 136, 1375-1384.
Qian et al., (2002), "Targeted drug delivery via the transferrin receptor-mediated endocytosis pathway," Pharmacol. Rev. 54, 561-587.
Tomiya et al., (2003), "Complex -type biantennary $N$-glycans of recombinant human transferring from Trichoplusia in cells expressing mammalian $\alpha$-1,4-galactotransferase and -1,4-$N$-acetylglucosaminenyltransferase II," Glycobiology 13, 23-34.
Janciauskiene, (2001), "Conformational properties of serine proteinase inhibitors (serpins) confer multiple pathophysiological roles," Biochim. Biophys. Acta 1535, 221-235.
Finlay et al., (1993), "$\alpha_1$ -Antitrypsin and anchorage-independent growth of MCF-7 breast cancer cells," Endocrinology 133, 996-1002.
Perraud et al., (1988), "Proliferation of rat astrocytes, but not of oligodendrocytes, is stimulated in vitro by protease inhibitors," Int. J. Devl. Neuroscience 6, 261-266.
She et al., (2000), "$\alpha_1$ -Antitrypsin can increase insulin-induced mitogenesis in various fibroblast and epithelial cell lines," FEBS Lett. 473, 33-36.
Dabbagh et al., (2001), "Alpha-1-antitrypsin stimulates fibroblast proliferation and procollagen production and activates classical MAP kinase signaling pathways," J. Cell. Physiol. 186, 73-81.

(Continued)

*Primary Examiner*—Laura B Goddard
(74) *Attorney, Agent, or Firm*—Faegre & Benson, LLP

(57) ABSTRACT

Compositions of human proteins, methods and regimens for reducing the occurrence and growth of skin cancer, including melanoma, are provided. The methods include steps of administering topically on the skin tumor or a skin cancer-free area of compositions containing therapeutically effective amounts of human alkaline phosphatase, transferrin and $\alpha$1-antitrypsin. In some embodiments, the composition is topically administered and includes all three proteins. Alkaline phosphatase, alone or in combination with transferrin and $\alpha$1-antitrypsin can also be administered by injection with or without simultaneous or sequential topical administration. Administration of compositions topically and/or by injection can be part of a more complex cancer therapy including chemotherapy, radiotherapy, surgery, and electrochemotherapy.

15 Claims, 2 Drawing Sheets

OTHER PUBLICATIONS

McKeehan et al., (1986), "Two apparent human endothelial cell growth factors from human hepatoma cells are tumor-associated proteinase inhibitors," J. Biol. Chem. 261, 5378-5383.

Graziadei et al., (1994), "The acute-phase protein α1-antitrypsin inhibits growth and proliferation of human early erythroid progenitor cells (burst-forming units-erythroid) and of human erythroleukemic cells (K562) in vitro by interfering with transferrin iron uptake," Blood 83, 260-268.

Moraga et al., (2001), "Effects of noninhibitory α-1-antitrypsin on primary human monocyte activation in vitro," Arch. Biochem. Biophys. 386, 221-226.

Niemann et al., (1997), "Inhibition of human serine proteases by SPAAT, the C-terminal 44-residue peptide from $\alpha_1$-antitrypsin," Biochem. Biophys. Acta 1340, 123-130.

Bergman et al., (1993), "Synthesis of $\alpha_1$-antichymotrypsin and $\alpha_1$-antitrypsin by human trophoblast," Pediatric Res. 34, 312-317.

Leicht et al., (1982), "Sequence homology and structural comparison between the chromosomal human $\alpha_1$-antitrypsin and chicken ovalbumin genes," Nature 297, 655-659.

Long et al., (1984), "Complete Sequence of the cDNA from human $\alpha_1$-antitrypsin and the gene for the S variant," Biochemistry 23, 4828-4837.

Kwon et al., (1994), "Single amino acid substitutions of $\alpha_1$-antitrypsin that confer enhancement in thermal stability," J. Biol. Chem. 269, 9627-9631.

Kataoka et al., (1999), "Enhanced tumor growth and invasiveness in vivo by a carboxyl-terminal fragment of $\alpha_1$-proteinase inhibitor generated by matrix metalloproteinases: A possible modulatory role in natural killer cytotoxicity," American J. Pathol. 154, 457-468.

Albino et al., (2000), "Cell cycle arrest and apoptosis of melanoma cells by docosahexanoic acid: Association with decreased pRb phosphorylation," Cancer Res. 60, 4139-4145.

Zhang et al., (2004), "Staurosporine induces apoptosis of melanoma by both caspase-dependent and -independent apoptotic pathways," Mol. Cancer Ther. 3, 187-197.

Weiss et al., (2003), "Inhibition of melanoma tumor growth by a novel inhibitor of glycosylceramide synthase," Cancer Res. 63, 3654-3658.

Ghosh et al., (1968), "Purification and properties of molecular-weight variants of human placental alkaline phosphatase," Biochem. J. 108, 779-792.

Chang et al., (1992), "Human placenta alkaline phosphatase: An improved purification procedure and kinetic studies," Eur. J. Biochem. 209, 241-247.

"Compounds and compositions to control abnormal cell growth," U.S. Appl. No. 11/458,502, filed Jul. 19, 2006.

* cited by examiner

ALKALINE PHOSPHATASE COMPOSITIONS TO REDUCE SKIN CANCER

FIELD OF THE INVENTION

This invention relates to the use of human alkaline phosphatase, such as placental alkaline phosphatase or transferrin alone or alkaline phosphatase in combination with transferrin, and, optionally, $\alpha_1$-antitrypsin to prevent or reduce the growth of skin cancer in mammals.

BACKGROUND

Over a lifetime there is an increasing potential for the development of skin cancer. It is estimated that over the lifetime 20% of United States population will develop skin cancer. A major external risk factor is sunlight. While basal cell and squamous cell carcinomas represent the majority of skin cancer cases, the leading cause of death due to skin cancer is malignant melanoma. There were 51,400 cases of melanoma in the United States in 2001, with 7800 deaths. The cure rates for basal cell and squamous cell carcinomas in developed countries is around 90% or higher. The prognosis for melanoma is less favorable; taking all age groups together, a little over 50% of patients with stage 1 disease (early stage disease) will survive 5 years free of recurrence. However, patients with disseminated disease have a median survival of less than 6 months. Clearly, of the various forms of skin cancers, malignant melanoma is the one that is the most dangerous.

Currently, the treatment of melanoma consists of local excision with a 0.5-1 cm surgical margin often associated with regional lymph node dissection. Other therapies, often combined with surgery, include radiotherapy, chemotherapy, immunotherapy (dendritic cells and immune vaccines), biological response modifiers (such as interleukin-2) and hypothermia. The treatment for other skin cancers consists of mainly surgical excision; other treatments include electrocautery and curettage, chemosurgery, cryosurgery, radiotherapy and topical chemotherapy. Each technique has advantages and disadvantages as listed in a recent article [Martinez, J.-C. and Otley, C. C. (2001), "The management of melanoma and nonmelanoma skin cancer: A review for the primary care physician," Mayo Clin. Proc. 76, 1253-1265]. Unlike many other cancers, malignant melanoma is notoriously resistant to chemotherapy. Also, while there is some evidence that melanoma may be treated with immune therapy, so far various vaccine therapies, cytokine therapy, or immune cell therapy (such as dendritic cell therapy) have met only with limited success. For example, in advanced melanoma cases only modest antitumor effects were reported with high doses of interferon (IFN)-α2b and interleukin-2, while several other cytokines were ineffective [Atkins, M. B., Elder, D. E., Essner, R., Flaherty, K. T., Gajewsky, T. F., Haluska, F. G., Hwu, P., Keilholz, U., Kirkwood, J. M., Mier, J. W., Ross, M. I., Slingluff, C. L., Sondak, V. K., Sosman, J. A., Weinstock, M. A. and King, L. (2006), "Innovations and challenges in melanoma: Summary statement from the first Cambridge conference," Clin. Cancer Res. 12 (7 Suppl), 2291s-2296s; Atkins, M. B. (2006), "Cytokine-based therapy and biochemotherapy for advanced melanoma," Clin. Cancer Res. 12 (7 Suppl), 2353s-2358s]. Furthermore, some cytokines, particularly interleukin-1β (IL-1β), actually promote tumor growth and metastasis [Elaraj, D. M., Weinreich, D. M., Varghese, S., Puhlmann, M., Hewitt, S. M., Carroll, N. M., Feldman, E. D., Turner, E. M. and Alexander, H. R. (2006), "The role of interleukin 1 in growth and metastases of human cancer xenografts," Clin. Cancer Res. 12, 1088-1096].

Another cytokine that can induce apoptotic cell death is tumor necrosis factor-α (TNF-α) normally produced by macrophages, T lymphocytes and endothelial cells upon inflammatory stimuli [Varfolomeev, E. E. and Ashkenazi, A. (2004), "Tumor necrosis factor: an apoptosis juNKie?," Cell 116, 491-497]. As it was recently reviewed [Benlloch, M., Mena, S., Ferrer, S., Obrador, E., Asensi, M., Pellicer, J. A., Carretero, J., Ortega, A. and Estrela, J. M. (2006), "Bcl-2 and Mn-SOD antisense oligodeoxynucleotides and glutamine-enriched diet facilitate elimination of highly resistant B16 melanoma cells by tumor necrosis factor-α and chemotherapy," J. Biol. Chem. 281, 69-79], recombinant TNF-α can induce hemorrhagic necrosis and regression of tumors including melanoma, and it is being utilized for the treatment of patients with locally advanced solid tumors. Unfortunately, delivery of optimal doses of TNF-α is associated with severe toxicity that restricts its administration to sub-optimal doses.

In view of the increasing incidence of skin cancer and the difficulty to treat disseminated melanoma, a large segment of the population would benefit from the use of an agent or a combination of agents capable of inhibiting early stage melanoma and reducing or preventing the occurrence of skin cancer. In order to avoid side effects and simplify the treatment, such agent(s) should preferably act locally on the skin. Presently no effective local treatment can be offered to prevent skin cancer or to treat melanoma patients. Pre-clinical studies performed by others suggest that locally applied inhibitors of Akt kinase and extracellular signal-regulated kinase may be introduced into the clinical practice at some future date [Bedogni, B., O'Neill, M. S., Welford, S. M., Bouley, D. M., Giaccia, A. J., Denko, N. C. and Powell, M. B. (2004), "Topical treatment with inhibitors of the phosphatidylinositol 3'-kinase/Akt and Raf/mitogen-activated protein kinase kinase/extracellular signal-regulated kinase pathways reduces melanoma development in severe combined immunodeficient mice," Cancer Res. 64, 2552-2560].

SUMMARY OF THE INVENTION

Responding to the need for effective prevention and control of melanoma and other skin cancers, embodiments of this invention describe the use of human placental alkaline phosphatase (PALP) or transferrin alone or in combination with transferrin (TF) and (optionally) $\alpha_1$-antitrypsin (AT) for prevention and treatment of skin cancer. The invention allows administration of compositions topically on the skin or by injection, or both.

Embodiments of this invention demonstrate the feasibility of using human proteins for topical treatment of mammalian skin to reduce both the occurrence and growth of skin cancer. Such topical treatment may be combined with application of these proteins by an injection method as well. Also, administration of protein compositions may be part of a more complex cancer therapy.

One of the human proteins used in an alternative embodiment of the invention is placental alkaline phosphatase (PALP) a member of the alkaline phosphatase family. In one embodiment, the invention provides methods to employ PALP, and by implication other alkaline phosphatases, in humans and other mammals via topical application to prevent the occurrence or decrease the growth of already existing abnormally growing skin tumor tissues. In another embodiment, alkaline phosphatase is delivered via injection directly into the dermis or skin tumor or by using other available injection methods to reduce the growth of already existing abnormally growing skin tumor tissues. In an additional embodiment, the alkaline phosphatase may be delivered simultaneously or sequentially by an injection method and topically to reduce the growth of skin tumor.

The other human proteins that can be used in combination with alkaline phosphatase in the embodiments for both topical and injection applications are human transferrin (TF) and human $\alpha_1$-antitrypsin (AT). In addition to PALP alone, the following combinations of proteins are demonstrated in alternative embodiments of the invention to exert antiskin-cancer effects upon topical application: PALP+TF and PALP+TF+AT. In view of the demonstrated anti-melanoma activities of TF and AT, the use of PALP+AT and TF+AT combinations for topical treatment of skin cancer is also within the scope of the invention. In addition, commercial PALP preparation that contains both TF and AT in addition to PALP may be used both topically and by an injection method.

Some embodiments of the invention use the above protein compositions either topically or by injection in combination with surgery, chemotherapy, radiotherapy and any other therapies that are already in clinical use or are being developed to control the growth of abnormally growing skin tumor cells.

DETAILED DESCRIPTION OF THE INVENTION

Definitions

Figure 1:
FIG. 1 shows a digital image of a gel separation, demonstrating that the PALP used for the experiments, except when indicated otherwise, was homogeneous or near homogeneous. The image also shows the protein composition of the starting commercial PALP preparation, the three major bands being represented by TF alone (80 kDa), a mixture of albumin and PALP (~66-68 kDa) at a ratio of approximately 3:1, and AT (52 kDa).

The term "PALP" refers generally to the full-length human alkaline phosphatase protein, including isoforms and any chemically modified versions such as created, for example, by glycosylation, phosphorylation, metal-binding, or ligand-binding. As used herein, PALP is not limited to only placental alkaline phosphatase, but also includes intestinal alkaline phosphatase, germ cell alkaline phosphatase, and tissue non-specific alkaline phosphatase (found in bone, liver, and kidney).

The phrase "active derivative of PALP" is intended to include any segment or region of PALP that alone or in conjunction with the other proteins promotes an anti skin-cancer effect.

The term "composition" refers to one or more compounds in various combinations according to alternative embodiments of this invention. The combinations include a single component of either PALP or TF, or two components, either PALP and TF, or PALP and AT, or TF and AT or all three components, PALP, TF and AT.

The term "administered" generally refers to administering the composition of PALP, TF, AT or various combinations as topical composition, injectable composition, or as a combination of a topical and injectable composition.

The term "sequential" or "simultaneously" refer to the administration of the composition simultaneously or sequentially but as separate a composition.

As used in this application, all percentages are weight percentages.

Active Compositions

The first active agent is human placental alkaline phosphatase (PALP) or an active derivative thereof. As used herein, the term "PALP" and the phrase "human PALP" are used interchangeably to refer to placental alkaline phosphatase. The phrase "active PALP" means the human protein and its glycosylated and non-glycosylated forms as well as peptides derived from these proteins that, when administered locally or by a systemic route reduces the growth of skin cancer cells in mammalian skin tumors in a well detectable manner.

PALP is a member of the alkaline phosphatase group of enzymes that hydrolyzes phosphate-containing compounds at alkaline pH. Mature PALP is a dimer of two identical glycosylated subunits. Each subunit has an approximate molecular weight of 66 kDa, as determined by gel electrophoresis.

The alkaline phosphatase family also includes the tissue non-specific (liver/bone/kidney) alkaline phosphatase, the intestinal alkaline phosphatase, and the PALP-like (germ cell) alkaline phosphatase. Since each of these enzymes has similar phosphatase activities that may contribute to the negative control of cancer cell growth, these three enzymes may share, at least partially, the anti-cancer effects of PALP.

It was reported earlier that placental alkaline phosphatase, one of the presently known four members of the alkaline phosphatase enzyme family, can enhance both the proliferation and survival of mouse embryo fibroblasts as well as fibroblast-like cells derived from the lung of human fetus [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167] [Q.-B. She, J. J. Mukherjee, T. Chung, and Z. Kiss (2000), "Placental alkaline phosphatase, insulin, and adenine nucleotides or adenosine synergistically promote long-term survival of serum-starved mouse embryo and human fetus fibroblasts," Cellular Signalling 12, 659-665].

In contrast, in the present application, PALP is used either alone or in combination with other human proteins to decrease the growth of melanoma in various melanoma models. For this, either commercial PALP was used, or PALP was highly purified from commercial (Sigma-Aldrich) PALP prepared by a slightly modified method described earlier [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167]. Analysis by gel electrophoresis sequence determination shows that in the PALP preparations purchased from Sigma-Aldrich and used for the work presented in embodiments of the invention, PALP on average represented about 10% of the total protein the remaining being represented by TF (12%), AT (30%), albumin (35%), and few other contaminating proteins mostly including proteolytic degradation products of TF (13%).

The exact mechanism by which PALP inhibits the growth of melanoma tumor in vivo is presently not known. PALP does not exhibit major inhibitory effects on the viability of melanoma cells in vitro. Accordingly, the effects of PALP on melanoma growth in vivo are likely to be mediated by indirect mechanisms such as, for example, activation of the anti-cancer components of the immune system or increased resistance of surrounding normal cells against tumor cells.

Digestion of PALP with the protease bromelain provided an active derivative [U.S. patent application Ser. No. 10/653,622, filed Sep. 2, 2003 and entitled "Use of Placental Alkaline Phosphatase to Promote Skin Cell Proliferation"; Pub. No. US2005/0048046 A1, Pub. Date, Mar. 3, 2005]. Consequently, one who is skilled in the art may synthesize or develop an active derivative that is a smaller fragment of a PALP amino acid sequence and demonstrates efficient inhibition of skin cancer growth similar to that obtained with native PALP. By way of example, modification of a PALP amino acid sequence or a sequence of smaller PALP peptides by exchanging amino acids at critical sites to yield an active derivative may also result in the maintenance or even improvement of the beneficial effects of PALP. Likewise, chemical or enzymatic changes in the level and position of glycosylation may maintain or enhance the effects of PALP or its derivatives. In the practice of embodiments of the invention, it is envisioned that modified PALP, smaller PALP-derived peptides, or modified PALP-derived peptides may be similarly effective or even more effective than the native PALP enzyme, and are each considered to be active derivatives. Likewise, PALP isolated from placenta tissue or produced in recombinant form is considered to be similarly effective.

Human PALP in solid form is available commercially from Sigma-Aldrich (St. Louis, Mo.), for example (Sigma catalog number P3895; CAS Registry Number 9001-78-9). Another commercial source of human PALP is Calbiochem (San Diego, Calif.; catalog number 524604).

Human PALP, and particularly an active derivative, may also be obtained by chemical synthesis using conventional methods. For example, solid-phase synthesis techniques may be used to obtain PALP or an active derivative.

Recombinant methods to obtain quantities of PALP (and active derivative) are also suitable. Since cDNA of PALP is available, recombinant protein can be produced by one of the many existing conventional methods for recombinant protein expression. PALP has been cloned and overexpressed in a mammalian cell line as described by Millan, et al. [Kozlenkow, A., Manes, T., Hoylaerts, M. F. and Millan, J. L. (2002), "Function assignment to conserved residues in mammalian alkaline phosphatase," J. Biol. Chem. 277, 22992-22999]. Production of recombinant PALP by bacteria [Beck, R. and Burtscher, H. (1994), "Expression of human placental alkaline phosphatase in *Escherichia coli*," Protein Expression and Purification 5, 192-197] and yeast [Heimo, H., Palmu, K. and Suominen, I. (1998), "Human placenta alkaline phosphatase: Expression in *Pichia pastoris*, purification and characterization of the enzyme," Protein Expression and Purification 12, 85-92] has also been reported.

Bacterial expression yields non-glycosylated PALP. So far there is no evidence that the anti-cancer effects of native glycosylated PALP and bacteria-produced PALP would be significantly different. Thus, in alternative embodiments of the methods, native glycosylated PALP and its active derivatives as well as non-glycosylated PALP and its active derivatives may be used interchangeably.

A PALP preparation that is commercially available contains other proteins that may be removed or may be retained depending on the delivery method and the purpose of application. Commercial PALP preparations can be used as starting material to obtain homogeneous PALP, transferrin (TF) and $\alpha_1$-antitrypsin (AT) by successive chromatographic steps, as described in detail in Example 1. Commercial PALP preparations may also be used for compositions used in the practice of embodiments of the present invention, so long as the given composition comprises therapeutically effective amount of PALP, TF and AT, and the other impurities are not toxic and do not interfere with the beneficial effects of these components. As it will be dealt with later, TF and AT add to the anti-skin cancer effects of PALP.

For applications by an injection method, PALP (as well as TF and AT) may be used only in a "highly purified" form. A raw extract of PALP should be treated to enrich the concentration of PALP and obtain a substantially purified or highly purified preparation. A highly purified preparation will have a much higher concentration of the active component than found in a raw tissue extract. A highly purified PALP preparation does not contain detectable amounts of other proteins or contains such a minimum amount of known contaminants that the benefits of using the preparation far out-weight the accompanying potential risks. The term "substantially purified" is used herein to encompass compositions that are obtained from a starting material by one or more purification steps (such as solvent extraction, column separation, chromatographic separation, etc.) that enrich the concentration of PALP, relative to the starting material, to an extent that PALP is the dominating component, and the remaining components do not pose any significant health risk and do not reduce the beneficial effects of PALP. The term "substantially purified" should not be construed to connote absolute purity.

The placenta-derived PALP-enriched preparation may contain TF and AT in sufficient or near sufficient amounts to support the anti-cancer effects of PALP. As demonstrated in various embodiments of the invention, a commercial preparation of PALP available from Sigma-Aldrich satisfies this criterion. Therefore, for the treatment of mammals either locally on the skin or by injection with the purpose of preventing or treating skin cancer the above-described commercial preparation of PALP may be applicable without further modification of the protein components. In other embodiments, the commercial PALP may be supplemented with various additives or enhancers to increase its anti-cancer effects. In still other embodiments, a step of heat-activation of PALP preparation may be included prior to either local or systemic application.

In some embodiments, preparation of PALP for either local or systemic treatment may include 1-3 mM of a calcium containing compound (for example, calcium chloride) and/or 1-50 μM of a zinc containing compound (for example, zinc chloride or zinc sulfate).

Substantially purified preparations of intestinal, tissue non-specific, and PALP-like (germ cell) alkaline phosphatase enzymes are all available commercially (for example, from Sigma-Aldrich). Appropriate purification methods are known for their isolation from human blood, liver, and other organs. Also, recombinant forms of each of these alkaline phosphatases have already been produced.

Transferrin

TF is the second potential component of a protein mixture developed for the prevention and treatment of skin cancer. TF is also a glycoprotein with an approximate molecular weight of 80 kDa. Its major function is to carry iron from the sites of intake into the systemic circulation to the cells and tissues.

However, TF also serves as a growth factor for many cell types including cancer cells; for this reason, it is a standard component of several growth media used for cell culture. Whether the growth factor effects of TF are always mediated by iron or not is presently unclear.

Melanoma is especially sensitive to oxidative stress [Baldi, A., Lombardi, D., Russo, P., Palescandolo, E., De Luca, A., Santini, D., Baldi, F., Rossiello, L., Dell'Anna, M. L., Mastrofrancesco, A., Maresca, V., Flori, E., Natali, P. G., Picardo, M. and Paggi, M. G. (2005), "Ferritin contributes to melanoma progression by modulating cell growth and sensitivity to oxidative stress," Clin. Cancer Res. 11, 3175-3183]. On the other hand, in many physiological conditions iron acts like a pro-oxidant. Chronic pro-oxidant stimuli can induce superoxide dismutase activity whereas catalase can be inactivated by $H_2O_2$, its own substrate. Such imbalance between superoxide dismutase and catalase activities results in surplus $H_2O_2$ formation which then, in the presence of iron, leads to generation of extremely reactive hydroxyl radicals via the Fenton reaction. In sum, excess intracellular iron, provided by excess transferrin, may overwhelm the cellular anti-oxidant systems leading to melanoma cell death. These facts led to consider TF as a potential agent that may negatively influence the growth of melanoma tumors.

Another potentially important property of TF is its ability to promote migration (but not proliferation) of endothelial cells [Carlevaro, M. F., Albini, A., Ribatti, D., Gentili, C., Benelli, R., Cermelli, S., Cancedda, R. and Cancedda, F. D. (1997), "Transferrin promotes endothelial cell migration and invasion: Implication in cartilage neovascularization," J. Cell. Biol. 136, 1375-1384]. By doing so, TF was expected to promote blood vessel formation in the tumor tissue. In turn, increased vascularization should facilitate distribution of proteins and chemotherapeutic agents in the tumor thereby increasing their efficiency.

The structure and biological effects of TF as well as the properties of transferrin receptor have recently been reviewed [Qian, Z. M., Li, H., Sun, H. and Ho, K. (2002), "Targeted drug delivery via the transferrin receptor-mediated endocytosis pathway," Pharmacol. Rev. 54, 561-587].

In several patent applications and patents, TF has been listed as a minor component of complex mixtures that may add to the effects of major promoters of skin rejuvenation and repair, without either specifying or directly proving such role [U.S. patent application Ser. No. 222,949, filed Apr. 10, 2003 and entitled "Composition and Methods for Skin Rejuvenation and Repair"; U.S. Pat. No. 5,461,030, issued Oct. 24, 1995 and titled "Compositions and Methods for Enhancing Wound healing"; U.S. Pat. No. 5,591,709, issued Jan. 7, 1997 and entitled "Compositions and Methods for Treating Wounds"; U.S. Pat. No. 5,556,645, issued Sep. 17, 1996 and entitled "Methods of Enhancing Wound Healing and Tissue Repair"; U.S. Pat. No. 4,347,841, issued Sep. 7, 1982 and titled "Biological Wound Covering and Method for Producing Same"]. TF has never been used alone or along with PALP and AT to control skin cancer growth.

As used herein, the term "TF" and the phrase "human TF" are used interchangeably to refer to transferrin. As used herein, active TF means the human protein, or closely related mammalian proteins, and its/their glycosylated and non-glycosylated forms as well as peptides derived from these proteins that, when administered alone or particularly together with PALP or PALP+AT is effective to decrease the growth of melanoma and, by implication, other skin cancers.

For these studies, TF was bought from Sigma-Aldrich (T 3309; 98% pure; 300-600 μg iron per g protein). Because TF is a major component of human blood, and placenta always contains significant volume of blood, the placenta tissue is also a potential source for the isolation of this protein. Chromatographic separation methods are available for the purification of TF from blood or placenta. For example, it is possible to enrich TF, along with some other glycoproteins such as PALP and AT, using a so-called Concanavalin-A-Sepharose column, which separates glycoproteins based on their ability to interact with lectins such as Concanavalin-A. This step may then be followed by other column chromatography methods, such as size-exclusion chromatography, to separate glycoproteins from each other. These techniques are well known in the art.

TF is also present (at the level of about 12% of total protein) in the commercial PALP preparation used for the purification of PALP and AT. Thus, TF can also be isolated in a highly purified state along with PALP and AT from commercial PALP.

The sequence of human TF (which has approximately 10 variants) is known and the corresponding cDNA is available. This allows expression of original TF or its point and deletion mutants in any cell line of choice, for example in insect cells [Tomiya, N., Howe, D., Aumiller, J .J., Pathak, M., Park, J., Palter, K. B., Jarvis, D. L., Betenbaugh, M. J. and Lee, Y. C. (2003), "Complex-type biantennary N-glycans of recombinant human transferrin from *Trichoplusia* in cells expressing mammalian β-1,4-galactotransferase and β-1,4-N-acetylglucosaminenyltransferase II," Glycobiology 13, 23-34]. These and similar techniques may be used to generate, at larger scale, various active recombinant forms of TF and its derivatives The stimulatory effects of TF on fibroblast proliferation in vitro are not altered by pre-heating it at up to 75° C. for 30 min. Thus, pre-heating of TF-containing compositions to enhance the effects of other components, such as PALP and AT will be unlikely to alter other effects of TF such as inhibition of melanoma growth.

Some TF preparations that are commercially available from Sigma-Aldrich contain some minor impurities (2-3% of the total protein). Such commercial TF preparations, including those that do not contain iron (apo-TF) or nearly saturated by iron (holo-TF) can be further purified by available methods to obtain homogeneous TF by successive chromatographic steps. Commercial TF preparations with relatively minor impurities may also be used in the practice of embodiments of the present invention, so long as the given composition comprises therapeutically effective amount of TF, and impurities are not toxic and do not interfere with the beneficial effects of the components. In embodiments of the invention, the commercial TF that was used (Sigma-Aldrich; catalog number, T 3309) was partially iron-saturated and practically did not contain endotoxin or other contaminating proteins. Such preparation may be used for both systemic and local applications without further purification.

If blood- or placenta-derived TF preparation are to be used in the practice of embodiments of the present invention, a raw extract or fraction should be treated to enrich the concentration of TF, with or without parallel enrichment of AT and/or PALP, and obtain a more purified preparation. A purified preparation will have a higher concentration of the active component than found in a raw tissue or blood extract. The term "purified" is used herein to encompass compositions that are obtained from a starting material by one or more purification steps (such as solvent extraction, column separation, chromatographic separation, etc.) that enrich the concentration of TF, relative to the starting material. The term "purified TF" should not be construed to connote absolute purity of the protein.

A further consideration in embodiments of the invention is the degree of purity that is required for the anti-cancer effect. An advantage of using a preparation comprising highly purified or homogeneous TF in the methods and treatment regiments of embodiments of the present invention is that possible side effects caused by contaminating proteins will not likely be an issue. However, impure TF or TF that is purified but not homogeneous also can be used in the compositions described herein, as long as no adverse effects are observed. Considering that every consecutive purification step, either using blood or placenta as starting material, results in some loss of the protein, using a less pure than homogeneous TF material for the compositions may be more cost-effective. As also mentioned above, isolation of less pure TF preparations that also contain optimal or near optimal amounts of PALP and AT may be more cost effective than assembling a preparation from highly purified TF, PALP and AT. As an example, the commercial PALP preparation used in embodiments of the invention contains effective amounts of TF, AT and PALP.

In some embodiments of the invention the TF preparation used to treat experimental melanoma was partially saturated with iron. However, it is within the scope of the embodiments of this invention to use either iron-free or iron-saturated TF to control skin cancer growth.

$\alpha_1$-Anti-Trypsin

The third potential active component in the methods and compositions of the present invention is human $\alpha_1$-antitrypsin (AT), or an active derivative thereof. As used herein, the term "AT" and the phrase human AT are used interchangeably to refer to $\alpha_1$-antitrypsin. As used herein, "active AT" means the various isoforms of the human protein, or closely related mammalian proteins, and its glycosylated and nonglycosylated forms as well as peptides derived from these proteins that can enhance the inhibitory effects of locally applied PALP and TF on the growth of skin cancer.

AT (in the literature also often called $\alpha_1$-proteinase inhibitor) belongs to the large family of serine protease inhibitors, or serpins, that act as irreversible suicide inhibitors of proteases [Janciauskiene, S. (2001), "Conformational properties of serine proteinase inhibitors (serpins) confer multiple pathophysiological roles," Biochem. Biophys. Acta 1535, 221-235]. While AT is a particularly effective inhibitor of elastase, it also inhibits other proteases such as trypsin.

AT was previously shown to inhibit the growth of breast cancer cells in vitro [Finlay, T. H., Tamir, S., Kadner, S. S., Cruz, M. R., Yavelow, J. and Levitz, M. (1993), "$\alpha_1$-Antitrypsin and anchorage-independent growth of MCF-7 breast cancer cells," Endocrinology 133, 996-1002]. As it will be demonstrated in the Examples, locally applied AT also slightly enhanced the inhibitory effects of PALP and TF on melanoma growth. PALP, TF and AT in combination were about as effective as the commercial PALP preparation which contains all these 3 proteins. In contrast to its inhibitory effects on cancer cells, AT was shown to stimulate proliferation of normal (healthy) cells [Perraud, F., Besnard, F., Labourdette, G. and Sensenbrenner, M. (1988), "Proliferation of rat astrocytes, but not of oligodendrocytes, is stimulated in vitro by protease inhibitors," Int. J. Devl. Neuroscience 6, 261-266; She, Q.-B., Mukherjee, J. J., Crilly, K. S. and Kiss, Z. (2000), "$\alpha_1$-Antitrypsin can increase insulin-induced mitogenesis in various fibroblast and epithelial cell lines," FEBS Lett. 473, 33-36; Dabbagh, K., Laurent, G. J., Shock, A., Leoni, P., Papakrivopoulou, J. and Chambers, R. C. (2001), "Alpha-1-antitrypsin stimulates fibroblast proliferation and procollagen production and activates classical MAP kinase signaling pathways," J. Cell. Physiol. 186, 73-81] including human endothelial cells [McKeehan, W. L., Sakagami, Y., Hoshi, H. and McKeehan, K. A. (1986), "Two apparent human endothelial cell growth factors from human hepatoma cells are tumor-associated proteinase inhibitors," J. Biol. Chem. 261, 5378-5383]. However, it was also reported that in human monocytes and reticulocytes AT inhibits binding of TF to its receptor thereby reducing proliferation and iron transport into these cells [Graziadei, I., Gaggi, S., Kaserbacher, R., Braunsteiner, H. and Vogel, W. (1994), The acute-phase protein $\alpha$1-antitrypsin inhibits growth and proliferation of human early erythroid progenitor cells (burst-forming units-erythroid) and of human erythroleukemic cells (K562) in vitro by interfering with transferrin iron uptake," Blood 83, 260-268]. Based on these controversial observations, one could not anticipate whether the individual stimulatory effects of TF and AT on mobility and proliferation of endothelial cells, respectively, will translate to increased capillary formation and decreased growth of melanoma, or the opposite will be observed. As it will be shown in the Examples, topical administration of commercial PALP (which contains PALP, TF and AT) in fact increased the formation of capillaries in the experimental melanoma tumor that was associated with decreased tumor growth.

It is relevant to embodiments of this invention that AT can be proteolytically degraded by metalloproteinases and serine proteases resulting in many cases in the formation of 36-44 amino acid cleaved forms. If the concentration of the 36 amino acid fragment reaches a critical value (above 1 μM), it can stimulate the production of tumor necrosis factor-$\alpha$ (TNF-$\alpha$) and interleukin-6 (IL-6) by monocytes [Moraga, F., Lindgren, S. and Janciauskiene, S. (2001), "Effects of non-inhibitory $\alpha$-1-antitrypsin on primary human monocyte activation in vitro," Arch. Biochem. Biophys. 386, 221-226]. In turn, these cytokines, particularly TNF-$\alpha$ may exert anti-tumor effects as it has been observed, for example, in melanoma tumors [Bennloch, M., Mena, S., Ferrer, S., Obrador, E., Asensi, M., Pellicer, J. A., Carretero, J., Ortega, A. and Estrela, J. M. (2006), "Bcl-2 and Mn-SOD antisense oligodeoxynucleotides and glutamine-enriched diet facilitate elimination of highly resistant B16 melanoma cells by tumor necrosis factor-$\alpha$ and chemotherapy," J. Biol. Chem. 281, 69-79]. Accordingly, it is within the scope of embodiments of the invention to use the above 36 or 44 amino acid or other active fragments of AT to enhance cytokine formation in the tumor. Such active fragments can be chemically synthesized using solid phase chemistry or other conventional methods [Niemann, M. A., Bagott, J. E. and Miller, E. J. (1997), "Inhibition of human serine proteases by SPAAT, the C-terminal 44-residue peptide from $\alpha_1$-antitrypsin," Biochim. Biophys. Acta 1340, 123-130] or they can be prepared from native AT by the protease elastase as reported [Moraga, F., Lindgren, S. and Janciauskiene, S. (2001), "Effects of non-inhibitory $\alpha$-1-antitrypsin on primary human monocyte activation in vitro," Arch. Biochem. Biophys. 386, 221-226].

Relatively pure AT is commercially available (for example, from Sigma-Aldrich; catalog number: A 9024), and it also can be highly purified from commercial PALP preparation which contains AT as a significant "contaminant." For the purpose of this application essentially pure AT, purified from commercial PALP preparation (Sigma-Aldrich) by a previously described method [She, Q.-B., Mukherjee, J. J., Crilly, K. S. and Kiss, Z. (2000), $\alpha_1$-Antitrypsin can increase insulin-induced mitogenesis in various fibroblast and epithelial cell lines," FEBS Lett. 473, 33-36] was used. Purification of AT is also described in the Examples. By implication, AT can be isolated in essentially pure form from human placenta. Placenta not only produces this protein [Bergman, D., Kadner, S. S., Cruz, M. R., Esterman, A. L., Tahery, M. M., Young, B. K.

and Finlay, T. H. (1993), "Synthesis of $\alpha_1$-antichymotrypsin and $\alpha_1$-antitrypsin by human trophoblast," Pediatric Res. 34, 312-317], but placenta-associated blood also is a rich source of AT.

As already mentioned above, commercial (Sigma-Aldrich) PALP may already contain an optimal amount of AT which effectively decreases the growth of skin cancer in the presence of PALP and TF.

The sequence of AT is known and the corresponding cDNA is available [Leicht, M., Long, G. L., Chandra, T., Kurachi, K., Kid, V. J., Mace, M. Jr., Davie, E. W. and Woo, S. L. C. (1982), "Sequence homology and structural comparison between the chromosomal human $\alpha_1$-antitrypsin and chicken ovalbumin genes," Nature 297, 655-659; Long, G. L., Chandra, T., Woo, S. L. C., Davie, E. W. and Kurachi, K. (1984), "Complete Sequence of the cDNA from human $\alpha_1$-antitrypsin and the gene for the S variant," Biochemistry 23, 4828-4837]. Molecular biology techniques are available to produce recombinant forms of AT, mutated forms of AT [Kwon, K.-S., Kim, J., Shin, H. S. and Yu, M.-H. (1994), "Single amino acid substitutions of $\alpha_1$-antitrypsin that confer enhancement in thermal stability," J. Biol. Chem. 269, 9627-9631] or smaller fragments of AT, or any other fragment of AT [Kataoka, H., Uchino, H., Twamura, T., Seiki, M., Nabeshima, K. and Koono, M. (1999), "Enhanced tumor growth and invasiveness in vivo by a carboxyl-terminal fragment of $\alpha_1$-proteinase inhibitor generated by matrix metalloproteinases: A possible modulatory role in natural killer cytotoxicity," American J. Pathol. 154, 457-468]. These and similar techniques may be used to generate various active recombinant forms of AT and its active derivatives.

The stimulatory effects of AT on fibroblast proliferation in vitro is enhanced by pre-heating it at 65-75° C. for 30 min or at 41° C. for 21 hours [She, Q.-B., Mukherjee, J. J., Crilly, K. S. and Kiss, Z. (2000), "$\alpha_1$-Antitrypsin can increase insulin-induced mitogenesis in various fibroblast and epithelial cell lines," FEBS Lett. 473, 33-36]. Thus, it is reasonable to assume that other biological effects of AT, such as inhibition of skin cancer growth, are also enhanced by heat treatment. Therefore, a step of heat-activation of AT may be included during the preparation of active compositions.

AT preparations that are commercially available contain impurities. Impure commercial AT preparations can be used as starting material to obtain homogeneous AT by successive chromatographic steps, as described in detail in Example 2. Impure AT preparations may also be used in formulating the compositions for use in the practice of embodiments of the present invention, so long as the given composition comprises therapeutically effective amount of AT, and impurities are not toxic and do not interfere with the beneficial effects of the components.

A preparation containing human AT may also be obtained by extraction from placental tissue that synthesizes the protein during pregnancy. By way of example, a preparation may be obtained by butanol extraction of homogenized placenta. Other methods of extraction from placental tissue are also suitable.

If blood- or placenta-derived AT preparation is to be used in the practice of embodiments of the present invention, a raw extract or fraction should be treated to enrich the concentration of AT and obtain a purified preparation. A purified preparation will have a higher concentration of the active component than found in a raw tissue or blood extract. The term "purified" is used herein to encompass compositions that are obtained from a starting material by one or more purification steps (such as solvent extraction, column separation, chromatographic separation, etc.) that enhance the concentration of AT, relative to the starting material. The term "purified AT" should not be construed to connote absolute purity of the protein.

A further consideration in the practice of the invention is the degree of purity that is required for the use in the anti-cancer compositions. In the methods of the invention, systemic application of AT will require a large degree of purification. For local application, the presence of other proteins (in addition to PALP and TF) and cell constituents in the AT preparation is acceptable as long as these contaminants do not cause any undesired side effects and do not decrease the effects of PALP, TF and AT.

Methods of Use

Embodiments of the present invention demonstrate that in animal skin cancer models both topical and subcutaneous application of highly purified PALP results in decreased skin tumor size. Human TF, alone or in combination with AT enhances the anti-skin cancer effects of PALP when applied topically on skin tumor. Furthermore, injected highly purified PALP adds to the inhibitory effects of topically applied commercial PALP preparation that contains significant amounts of TF and AT. Injected purified PALP also increases the effects of chemotherapy; this implies that topically applied PALP or mixtures of PALP+TF and PALP+TF+AT also exert similar additive effects with chemotherapy.

Both systemic and local administration of TF, but not AT, alone also resulted in decreased melanoma growth. Upon local administration, the combined inhibitory effects of PALP+TF and PALP+TF+AT were greater than the effects of TF or PALP alone.

Local Treatment of Melanoma:

In one embodiment, commercial PALP or a similar preparation assembled from highly purified PALP+TF+AT is dispersed in a suitable carrier and applied locally on the skin. The carrier used in some embodiments of the invention is *Vaselinum cholesteratum*. Other embodiments of the compositions include, for example, creams, gels, lotions, unguents, emollients, colloidal dispersions, suspensions, emulsions, oils, sprays, foams, mousses, and the like. Compositions suitable for topical application may also include, for example, liposomal carriers made up of lipids or special detergents.

Therapeutically effective amounts of commercial PALP or a similar composition composed of purified PALP, TF and AT may be used as the active components in the compositions described for local applications herein. Alternatively, preparations containing synthetic PALP, TF and AT or their active derivatives, or recombinant PALP, TF and AT or their active derivatives, may be employed as the active components. The term "active" means that the given component (as specified above) alone or in combination with the two other components exerts anti-skin cancer effect measured as decreased tumor volume and tumor mass. The term "therapeutically effective amount" in this specification indicates a dosage of an individual component that is effective in exerting a detectable anti-skin cancer effect either alone or in the presence of the other two components. The term "anti skin-cancer effect" is used in relation to cancer treatment describing a detectable and quantifiable reduction in the tumor volume and tumor mass. The term "preventive anti-skin cancer effect" is used in relation to cancer prevention expressing a reasonable expectation that if an agent is able to decrease skin cancer growth, the same agent will also be able to reduce the occurrence of skin cancer if used regularly to treat the cancer-free skin.

Compositions suitable for topical application in the practice of embodiments of the present invention generally include commercial PALP or similar preparations assembled from purified components as minor ingredient, and the physiologically compatible carrier as a major ingredient. "Commercial PALP" is defined as a preparation that can be purchased from a commercial firm and that contains, as the minimum, well detectable amount of PALP. Commercial PALP may also contain TF, AT, albumin, and minor contaminant proteins that do not interfere with the actions of PALP, TF and AT on skin tumor growth. The PALP preparation available from Sigma-Aldrich is a suitable preparation because (i) it contains PALP, TF, and AT, each contributing to the anti skin cancer effect, and (ii) the other proteins that are present do not interfere with the anti skin-cancer effects of PALP, TF, and AT.

In some embodiments, the compositions may include one or more additives or enhancers, such as preservatives, biologically active compounds with positive effects on normal skin cells and adverse effects on skin tumors, buffers, moisture-control compounds, or antibiotics, for example. In other embodiments, the composition contains the carrier and the active proteins.

A carrier may be in any form appropriate for topical application to the skin. Any physiologically compatible carrier in which the active components are at least minimally soluble is suitable for topical compositions in embodiments of the present invention. A physiologically acceptable carrier for the proteins is one that is non-toxic, does not elicit an adverse physical reaction upon administration, and in which the active component is sufficiently soluble so that the composition may provide an effective amount of the active component. The carrier should also provide the composition an appropriate consistency for topical administration and should be capable of achieving proper distribution of the active component to the treated tissue. In the preparation of carrier-active component mixture, the proteins can be first dissolved in water or a suitable buffer and then mixed with the carrier.

Suitable carriers generally include, for example, water, acetone, ethanol, ethylene glycol, propylene glycol, butane-1,3-diol, isopropyl myristate, isopropyl palmitate, mineral oil, mixtures thereof, and the like. Buffered solutions and physiological saline can also serve as carriers.

In some embodiments, the topical composition is a gel. The gel may include as a carrier methylcellulose, sepharose, agar, Vaseline or petrolatum, agarose, gelatin, dextran, dextran-polyethylene, polyhydroxyethylmethacrylate, hydrophilic cellulose polymer, polyethylene glycol, polyvinylpyrrolidine, amylose, polyethyleneoxide, calcium alginate, or combination thereof. By way of example, the proteins can be incorporated into sterile 3% by weight methyl cellulose gel, 1% by weight agarose gel, 4% by weight gelatin gel, or 1 to 3% by weight calcium alginate. One having ordinary skill in the art will have the knowledge to vary these components to obtain sustained release of the active component.

In some gel compositions, the carrier is *Vaselinum flavum* (yellow petrolatum), *Vaselinum album* (white petrolatum), or *Vaselinum cholesterinatum*. Commercially available *Vaselinum cholesterinatum* consists of about 1.5 wt.-% cholesterol, about 5.0 wt.-% cerae lanae, and about 93.5 wt.-% *Vaselinum flavum*.

Additives or enhancers may be included in the topical protein-containing compositions. The criterion for using an additive is that it increases, or at least does not decrease, the effectiveness of the active components in achieving the desired beneficial effect. Additives or enhancers in compositions for topical applications may include various ingredients, for example, preservatives (such as parabens, quaternary ammonium compounds, alcohols, phenols, essential oils, and the like), buffers, antioxidants (such as vitamin E), antimicrobials, vitamins, nutrients (such as essential and non-essential amino acids, choline, inositol, minerals, trace metals, salts, nucleosides, purines, pyrimidines, monosaccharides, disaccharides, carbohydrates) and moisture-control agents (such as glycerine, propylene glycol, and the like). Other potential additives include, for example, analgesics, anesthetics, emulsion stabilizers, preservatives, waterproofing agents, viscosity modifying agents, and the like.

The PALP/TF/AT-containing compositions can also be enhanced by other locally acting anti-cancer agents. As an example only, inhibitors of Akt kinase and extracellular signal-regulated kinase may be used for that purpose [Bedogni, B., O'Neill, M. S., Welford, S. M., Bouley, D. M., Giaccia, A. J., Denko, N. C. and Powell, M. B. (2004), "Topical treatment with inhibitors of the phosphatidylinositol 3'-kinase/Akt and Raf/mitogen-activated protein kinase kinase/extracellular signal-regulated kinase pathways reduces melanoma development in severe combined immunodeficient mice," Cancer Res. 64, 2552-2560].

In certain embodiments, the composition includes a penetration-enhancing additive that enhances penetration of proteins into the skin and tumor tissue. Many conventional penetration enhancers are suitable in the practice of the invention. Non-limiting examples of suitable penetration enhancers include: sulfoxides such as dimethyl sulfoxide (DMSO); alcohols such as ethanol; polyols such as propylene glycol; surfactants such as sodium lauryl sulfate, lecithin, docusate sodium, and polysorbates; fatty acids such as lauric acid, myristic acid, palmitic acid, mineral oil, and stearic acid; esters such as isopropyl palmitate and isopropyl myristate; and amides such as urea.

Embodiments of the present invention also provide protein-containing compositions suitable for transdermal administration. Such compositions are applied directly to the skin or incorporated into a protective carrier such as a transdermal device, i.e. a patch. Examples of suitable creams, ointments, or the like, can be found, for example, in the Physician's Desk Reference. Examples of suitable transdermal devices are described in, for example, U.S. Pat. No. 4,818,540 to Chien et al. entitled "Transdermal Fertility Control System and Process", incorporated herein by reference.

The protein-containing compositions can be made using a number of suitable techniques. In some embodiments, the proteins, optional additives and enhancers as well as a carrier are mixed together within a commercial mixer to form a solution, a suspension, a gel, or the like. All conventional methods known in the art for mixing may be suitable. Various equipment are also available to manufacture liposomal preparations (which provide for controlled, sustained release of the components). In pharmaceutical composition embodiments, methodologies for the formulation are well known, and can be found, for example, in Remington's Pharmaceutical Sciences, Eighteenth Edition, A. R. Gennaro, Ed., Mack Publishing Co. Easton, Pa. 1990, incorporated hereby by reference. The compositions may be additionally processed before and after formulation. Sterilization, for example, may be conducted individually by filter sterilization, while the whole composition can be irradiated or heat-treated or the like. Methods for conducting these steps are also conventional in the art.

In an embodiment, the protein-containing gel or other composition that is suitable to treat skin cancer comprises therapeutically effective amounts of PALP or an active derivative thereof, TF and AT or their active derivatives. Therapeutically effective amounts of active proteins may vary depending on the stage of skin cancer development, the needs or tolerance of the individual subject, and the nature of the other treatment(s).

Generally, the concentration of the individual active protein component in a composition for topical application will be at least about 0.01 wt.-%, and more suitably, between about 0.1 and about 4 wt.-% so that the total protein concentration does not exceed 6 wt.-%. As an example only, a suitable composition for local application contains 0.4% PALP, 0.5% TF, and 1.5% AT. Other suitable compositions may contain 0.1% to 2% commercial PALP.

Depending on the goal of the local application (i.e. if the goal is prevention or cancer treatment), the size of the tumor, the nature of other treatments, and other circumstances as evaluated by the clinician, several variants of the above compositions may be produced including those containing only PALP, TF, or PALP+TF. As an example only, PALP alone may be used for prevention, while a composition (such as commercial PALP) also containing TF and AT is recommended for the treatment of skin cancer.

The methods described here are suitable for mammals. The subject can be, for example, canine, porcine, equine, bovine, or human.

Embodiments of the invention also provides regimens for treating skin cancer comprising periodically administering by topical application to the skin specific compositions containing effective amounts of PALP, TF and AT or their active derivatives.

Generally, therapeutically effective amounts of the active components are administered. In the regimen of the invention, however, the effective amounts of the individual active components that are administered need not to be identical for each separate administration. More or less of the individual active component may be administered in separate administrations, as the subject's needs dictate. A medical professional supervising the treatment may adjust the administered dose of the total composition and the ratio of the individual components in it to obtain the desired results. An important consideration is that the therapeutically effective amount of the composition also depends on the nature and frequency of other treatments. For example, if the subject is treated with both the composition and chemotherapy, the effective tolerated dose of the former may be less compared to the situation when the subject is treated with the protein composition alone.

In one embodiment, the composition is applied topically to an area of cancer-free skin. In another embodiment, the composition is applied topically to an area of the skin cancer. In both cases, the composition is applied periodically over a period of time. As used with respect to the regimens described herein, the term "periodically" refers to repeated administration of the same or different compositions targeted at the cancer-free skin or skin cancer tissue over the time of treatment. The term "periodically" includes repeated administration at fixed intervals, but also includes repeated administration over irregular intervals as is required by the subject's condition. The frequency of administration of the composition(s) can vary depending on the type and size of skin cancer, the nature of other treatments, and the level of success. The frequency of application is less if the composition is used for prevention; for example, for preventive purpose once a week application is suitable. More frequent application is needed if a skin cancer is detected. In this case, the composition(s) can be administered two or more times a day, or once a day, or three-times a week. In one recommended embodiment of the regimen for the treatment of skin cancer, the same composition is applied once per day for a time period determined by the level of success.

Treatment of Melanoma with Injected Proteins Via One of the Available Routes.

Injection application here is defined as administration of anti-skin cancer agents by injection via any of the available routes to raise their amount in the tumor. Some injection methods (intravenous, intraarterial, intraportal, intraperitoneal) primarily increase the amount of injected material in the blood followed by redistribution into the tumor. Some other injection applications (intradermal, subcutaneous, intratissue, intracranial) lead to an increase in the amount of injected material both in the interstitial space close to the injection site and the vascular system.

As it will be demonstrated in the Examples, subcutaneously injected PALP alone was able to reduce the growth of melanoma and it further enhanced the inhibitory effects of topically applied commercial PALP. Highly purified PALP (16 mg/kg), injected into mice 15-times over a 3 weeks period, has not caused any significant pathological effects (cell death or immune cell infiltration) in the liver, lung, heart, blood, kidney, muscle, brain, spleen, and intestine. Injected highly purified PALP also failed to enhance metastasis of melanoma cells into the lung (see TABLE 6 in the Examples).

As reported in embodiments of this invention, subcutaneously injected TF alone enhances the number of metastatic tumors in the lung in the B16 melanoma model (TABLE 6). For this reason, even though short-term treatment with injected TF reduced the growth of melanoma, the use of injected TF alone for the control of skin cancer is not recommended except in extreme cases when survival of the cancer patient is more important that possible stimulation of metastasis.

Commercial PALP (60 mg/kg), injected into mice three-times a week over a one month period has not caused significant pathological effects in the liver, lung, heart, blood, kidney, muscle, brain, spleen, and intestine (data not shown). Injected commercial PALP also did not increase metastasis of melanoma cells into the lung (see TABLE 6 in the Examples), despite the presence of TF. The possible reason for this is that AT, a significant component of commercial PALP preparation, or PALP blocks the biological effect of TF required for increased metastasis. In support of this possibility, in certain cell lines AT was found to interfere with the function of transferrin receptor [Graziadei, I., Gaggi, S., Kaserrbacher, R., Braunsteiner, H. and Vogel, W. (1994), "The acute-phase protein $\alpha_1$-antitrypsin inhibits growth and proliferation of human early erythroid progenitor cells (burst-forming units-erythroid) and of human erythroleukemic cells (K562) in vitro by interfering with transferrin iron uptake," Blood 83, 260-268]. Overall, the evidence indicate that similar to highly purified PALP, commercial PALP, or a composition composed of PALP, TF and AT may also be used by an injection method for the control of melanoma growth.

For simplicity, in the following description the term "PALP" is used interchangeably for commercial PALP and for compositions that contain PALP plus TF at about 1:1 ratio or PALP+TF+AT with a ratio of about 1:1:5, respectively.

The injectable form of the composition is comprised of a therapeutically effective amount of PALP or an active derivative thereof as well as a physiologically acceptable carrier that does not cause an undesirable physiological effect and is capable of ensuring proper distribution of the active component in the melanoma tissue. The proteins are dissolved or dispersed in the physiologically acceptable carrier. Examples of carriers include physiological saline and phosphate-buffered saline. Alternatively, the protein(s) may be enclosed in liposomes such as immunoliposomes, or other delivery systems or formulations that are known to the art may be employed. By way of example, the active protein component(s) can be readily dissolved in physiological saline (0.9% NaCl), or in any other physiologically competent carrier, to yield a solution for injection. One suitable composition for the practice in the method comprises PALP in a 0.9% physiological salt solution to yield a total protein concentration of 10 mg/ml. Another suitable composition comprises PALP in a 0.9% physiological salt solution to yield a total protein concentration of 200 mg/ml. A composition comprising the active protein component(s) may be administered by one of the injection methods including, intravenous, intraperitoneal, subcutaneous, intraarterial, intradermal, intratumor, intracranial or intramuscular applications.

Various forms of injections can be used without other forms of treatment. However, injection of PALP-containing composition may be complementary to the topical treatment with the compositions described above to treat skin cancer. Treatments with injected and topically administered protein compositions may be applied simultaneously and sequentially with either the injection procedure or topical treatment applied first.

The injectable composition may be supplied with additives and enhancers that may be dissolved or suspended in the composition and that are expected to promote the anticancer effects of the proteins or diminish any potential side effect. Any chemotherapeutic agents already in clinical use such as, for example, dacacarbazine, cisplatin, vinblastin, doxorubicin, interferon alfa-2b, interleukin-12, taxol, bortezomib (PS-341) or tumor necrosis factor-α may be added as an enhancer. Similarly, any inhibitor of melanoma cell growth that is still in clinical trial may also be used as enhancers. As examples only, the list of such inhibitors includes docosaheaxanoic acid [Albino, A. P., Juan, G., Traganos, F., Reinhart, L., Connolly, J., Rose, D. P. and Darzynkiewitz, Z. (2000), "Cell cycle arrest and apoptosis of melanoma cells by docosahexanoic acid: Association with decreased pRb phosphorylation," Cancer Res. 60, 4139-4145], staurosporine [Zhang, X. D., Gillespie, S. K. and Hersey, P. (2004), "Staurosporine induces apoptosis of melanoma by both caspase-dependent and -independent apoptotic pathways," Mol. Cancer Ther. 3, 187-197], and inhibitors of glycosylceramide synthase [Weiss, M., Hettmer, S., Smith, P. and Ladisch, S. (2003), Inhibition of melanoma tumor growth by a novel inhibitor of glycosylceramide synthase," Cancer Res. 63, 3654-3658]. As reported in the Examples, CCDTHT, pyrrolidinethiocarbamate, zinc chloride and similar compounds add to the anti-skin cancer effects of PALP and they may also be used as enhancers. In one embodiment of the method, the mode of injection is selected from intravenous, subcutaneous, intraperitoneal intramuscular, intraarterial, intracranial, intradermal, or intratumor. The preferred modes of injection are intradermal or subcutaneous near the skin tumor or directly into the tumor that provides more optimal delivery of proteins to the skin tumor.

A common way to express a suitable dosage for systemic administration is grams of the active agent(s) per square meter of body surface area for the subject. Those having ordinary skill in the art are familiar with the formulas used for estimating a human subject's body surface area, based on the human's height (in cm) and mass (in kg).

In case of intravenous, intraarterial, intramuscular, intraperitoneal, intracranial or subcutaneous application, the subject may be administered a total of about 0.02 to 2.5-g PALP per $m^2$ body surface once daily. In another embodiment, a subject may be administered by intravenous, intraarterial, intramuscular, intraperitoneal, intracranial or subcutaneous application a total of about 0.02 to 2.5-g PALP per $m^2$ body surface twice or three times weekly. Alternatively, the subject may be administered a total of about 0.02 to 2.5-g PALP per $m^2$ body surface once a week or biweekly by intravenous, intraarterial, intramuscular, intraperitoneal, intracranial or subcutaneous application. Since the half-life time of PALP is long (5-6 days), a preferred application is twice a week or once a week.

One suitable treatment of skin cancer is by intradermal or intratumoral injection of the chosen composition(s). In both methods, for one injection site the subject may be administered a total of about 0.01 to 1 mg of active protein(s). Intradermal or intratumoral delivery of the composition can be performed once or twice daily, two-to-three times a week, once a week, or biweekly, as suitable.

If the chosen composition is injected locally, such as when the mode of injection is intradermal or intratumoral, aliquots of about 10 to 100 µL per injection site may be administered. The concentration of active protein(s) in the injectable composition may be in the range of about 0.1 to 50 mg/mL. Alternatively, the concentration of the active protein may be in the range of about 0.5 to about 20 mg/mL. In one embodiment, a plurality of injection sites is treated for one administration.

Concerning the effective tolerable dose, an important consideration is whether the proteins are used alone or used as part of a more complex regimen involving other anticancer agents as well. Such regimens may include any other treatment (for example, chemotherapy, radiotherapy, electrochemotherapy, surgery, treatment with immune vaccines, etc.) used to control skin cancer. Thus, if the subject is simultaneously or alternatively treated with a topically applied protein composition or an entirely different therapy, the effective tolerated amount of the injected protein(s) may be less compared to a regimen when the subject is treated with the protein(s) alone.

EXAMPLES RELATING TO THE METHODS USED

Example 1

Purification and Spectrophotometric Assay of PALP

Human PALP (Type XXIV, 1020 units of total activity) in a partially purified form was obtained commercially from Sigma-Aldrich. According to information received from the technical service of Sigma-Aldrich, their marketed PALP product (used here) was prepared by the method of Ghosh and Fishman [Ghosh, N. K. and Fishman, W. H. (1968), "Purification and properties of molecular-weight variants of human placental alkaline phosphatase," Biochem. J. 108, 779-792]. Briefly, the purification steps described in that paper involve homogenization of human placenta in Tris, extraction with butanol, exposure to heat (55° C.), three successive precipitations of protein with ammonium sulfate followed by re-suspension, fractionation with ethanol twice, and Sephadex-G-200-gel filtration optionally followed by continuous curtain electrophoresis to further separate PALP variants.

As determined by sodium dodecyl sulfate-polyacrylamide gel electrophoresis (SDS-PAGE) and peptide sequence analysis, the partially purified PALP obtained from Sigma-Aldrich was not homogeneous and contained other proteins. FIG. 1 shows a picture of a gel separation of a preparation comprising commercial PALP without further purification, and other preparations of PALP of increasing purity. Separation of proteins was performed by conventional SDS-PAGE, and proteins were stained with coomassie blue stain. Lane 1 contains various molecular mass standards for comparison. Lane 2 represents a preparation containing commercial PALP with a strong 52 kDa band representing AT and another strong 66-68 kDa band representing a mixture of PALP and albumin. The upper, ~80 kDa band is represented by TF. Lanes 3 and 4 represent preparations comprising commercial PALP material after further purification steps (described below), and lane 5 represents a preparation of homogeneous PALP obtained by the complete purification procedure described below.

A purification procedure was performed to further purify the commercially obtained PALP to homogeneity. A slightly modified procedure described earlier [She, Q.-B., Mukherjee, J. J., Huang, J.-S., Crilly, K. S. and Kiss, Z. (2000), "Growth factor-like effects of placental alkaline phosphatase in human and mouse embryo fibroblasts," FEBS Lett. 469, 163-167] was used which is incorporated herein by reference. The solution of commercial PALP was prepared by dissolving 350 mg of commercial PALP into 10 ml of buffer A (0.1 M sodium acetate, 0.5 M NaCl, 1 mM $MgCl_2$, 1 mM $CaCl_2$, adjusted to pH 6.5). This solution was then further purified by successive Concanavalin A-Sepharose and Q-Sepharose chromatography as indicated earlier by Chang et al. [Chang, T.-C., Huang, S.-M., Huang, T.-M. and Chang, G.-G. (1992), "Human placenta alkaline phosphatase: An improved purification procedure and kinetic studies," Eur. J. Biochem. 209, 241-247] followed by t-butyl hydrophobic interaction chromatography as described by She et al. [She, Q.-B., Mukherjee, J. J., Huang, J.-S., Crilly, K. S. and Kiss, Z. (2000), "Growth factor-like effects of placental alkaline phosphatase in human and mouse embryo fibroblasts," FEBS Lett. 469, 163-167] except that this last step was repeated in about 60% of cases (to eliminate traces of contaminant protein) in the invention.

First, the PALP solution was passed through a Concanavalin A-Sepharose column followed by an elution step using buffer A (50 mM α-methyl-D-mannopyranoside) as solvent. The active fractions collected from the effluent were pooled and dialyzed against buffer B (50 mM Tris-HCL at pH 7.7). SDS-PAGE separation of the collected and dialyzed fraction is shown in FIG. 1 in lane 3.

The collected and dialyzed fraction from the previous step was then passed through a Q-Sepharose column. The fraction of interest was eluted with buffer B using a linear gradient of 0-250 mM potassium phosphate at a pH of 7.5. The active fractions from the Q-Sepharose column were pooled and dialyzed against phosphate-buffered saline and concentrated by Amicon ultrafiltration. SDS-PAGE separation of the collected and dialyzed fraction is shown in FIG. 1 in lane 4, which demonstrates that at least two major proteins are still present in the fraction after dialysis.

Then, the collected and dialyzed fraction from the previous step was purified to homogeneity by t-butyl hydrophobic interaction chromatography (HIC). Prior to adding the fraction to the t-butyl HIC column, the fraction was made 2 M in ammonium sulfate, and the pH was adjusted to 6.8. The 5-ml bed volume t-butyl HIC cartridge (BIO-RAD, Hercules, Calif.) was connected to a fast performance liquid chromatography (FPLC) system from PHARMACIA (Peapack, N.J.). The fraction was introduced to the HIC column, and the column was eluted with buffer C (100 mM sodium phosphate buffer, 2 M ammonium sulfate at pH 6.8). The column was eluted with buffer C until a first protein-containing fraction completely eluted, and then a negative gradient of 2 M-to-0 M ammonium sulfate in 100 mM sodium phosphate at pH 6.8 was passed over the column. The negative linear gradient was used to elute a second protein-containing fraction, which contained the enzymatically active PALP protein.

The enzymatically active PALP fraction from the HIC separation was dialyzed against phosphate buffered saline and concentrated by Amicon ultrafiltration. The presence and purity of the PALP enzyme in the fraction was confirmed by SDS-PAGE. After electrophoretic separation, the gel was stained using coomassie blue or silver stain for visual observation of protein bands. When a single protein band with an approximate molecular weight of 66 kDa was not observed, the last chromatographic step was repeated. The pure PALP was further identified by sequence analysis performed by the Mayo Clinic Protein Core Facility (Rochester, Minn., US).

PALP enzyme activity was assayed using a spectroscopic method by monitoring the hydrolysis of 4-nitrophenylphosphate (as an increase in absorbance at 410 nm) at room temperature (22° C.) as described in Chang, G.-G., Shiao, M.-S., Lee, K.-R. and Wu, J.-J. (1990), "Modification of human placental alkaline phosphatase by periodate-oxidized 1,$N^6$-ethenoadenosine monophosphate," Biochem. J. 272, 683-690. Activity analysis of 5-10 μg purified enzyme was performed in 1 mL incubation volume containing 50 mM $Na_2CO_3/NaHCO_3$, 10 mM $MgCl_2$, 10 mM 4-nitrophenylphosphate at pH 9.8. The extinction coefficient of 4-nitrophenol was taken as $1.62 \times 10^4$ $M^{-1}$ $cm^{-1}$. An enzyme activity of 1 U (unit) is defined as 1 μmol substrate hydrolyzed/min at 22° C. at pH 9.8

Example 2

Purification of AT

A partially purified human placental alkaline phosphatase preparation was acquired from Sigma-Aldrich, Inc. AT is a major component of the commercially obtained PALP. AT was first further purified by successive Concanavalin A-Sepharose and Q-Sepharose chromatography as described by Chang et al. for the isolation of PALP [Chang, T.-C., Huang, S.-M., Huang, T.-M. and Chang, G.-G. (1992), "Human placenta alkaline phosphatase: An improved purification procedure and kinetic studies," Eur. J. Biochem. 209, 241-247]. The Q-Sepharose fraction, which still contained placental alkaline phosphatase in addition to AT, was further purified to homogeneity by t-butyl HIC chromatography [She, Q.-B., Mukherjee, J. J., Crilly, K. S. and Kiss, Z. (2000), "$α_1$-Antitrypsin can increase insulin-induced mitogenesis in various fibroblast and epithelial cell lines," FEBS Lett. 473, 33-36]. The 5 ml bed volume t-butyl HIC cartridge was connected to a PHARMACIA FPLC system and the fractions containing AT were pooled. The purity was confirmed by SDS-PAGE (polyacrylamide gel electrophoresis) using coomassie blue stain. The purified protein was identified as AT by sequence analysis. The sequence analysis was performed by the Mayo Clinic Protein Core Facility (Rochester, Minn., USA). The protein concentration was determined by the Lowry assay, using bovine serum albumin as standard, with a protein assay kit from Sigma-Aldrich, Inc. according to the instructions. This purification procedure has been previously published [She, Q.-B., Mukherjee, J. J., Crilly, K. S. and Kiss, Z. (2000), "$α_1$-Antitrypsin can increase insulin-induced mitogenesis in various fibroblast and epithelial cell lines," FEBS Lett. 473, 33-36].

Figure 2:
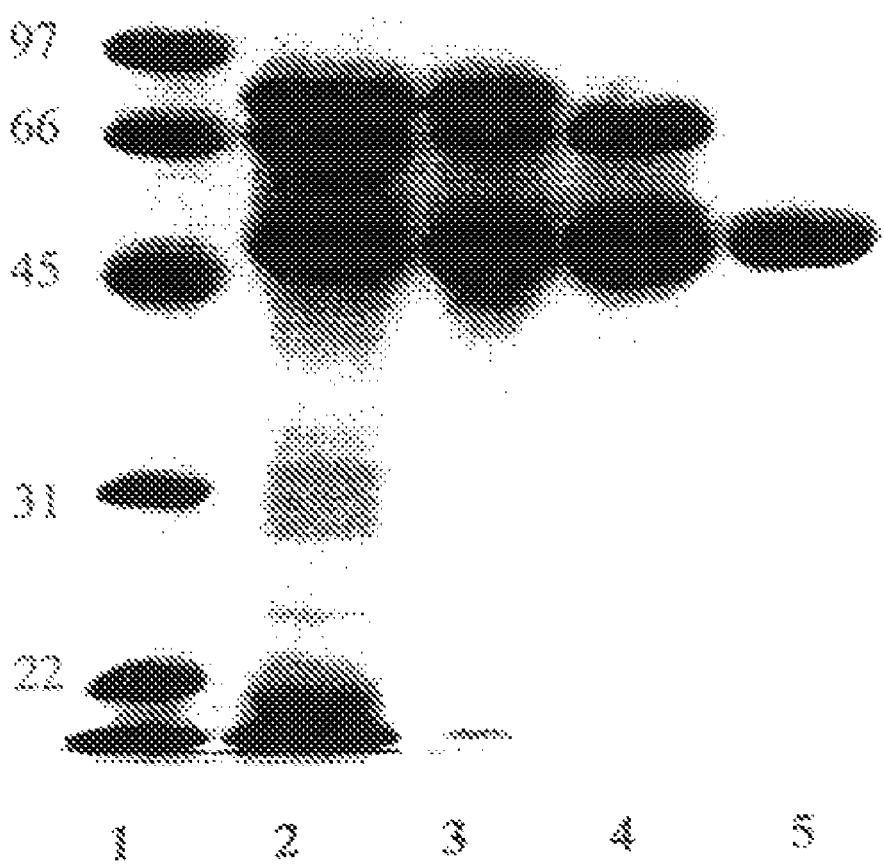
FIG. 2 shows a digital image of a gel separation, demonstrating that the $\alpha_1$-antitrypsin used for the experiments, except when indicated otherwise, was homogeneous, i.e. did not contain any other stained component. The image also shows that the protein composition of the starting commercial PALP preparation is slightly different compared to the starting material used for FIG. 1. Here, in addition to the three major bands, represented by TF (80 kDa), a mixture of albumin and PALP (66-68 kDa), and AT (52 kDa), there were several minor lower molecular weight proteins as well represented by $\alpha_1$-acid glucoprotein (~43 kDa) and degradation products of TF.

FIG. 2 is an image of a stained gel. The gel includes the commercially obtained partially purified placental alkaline phosphatase preparation (shown in lane 2) further purified by successive Concanavalin A-Sepharose (lane 3), Q-Sepharose (lane 4), and t-butyl HIC chromatography using 2 M-to-0 M ammonium sulfate gradient (lane 5). Lane 1 contains molecular mass standards of 97 kDa (top), 66 kDa, 45 kDa, 31 kDa, and 22 kDa (bottom) in that order. FIG. 2 demonstrates that while the commercially obtained preparation contains three major protein bands (one of them is represented by AT as indicated by the arrow, while a ~66-68 kDa band represents placental alkaline phosphatase+albumin) and several minor proteins, the purified preparation contains only AT. The upper, about ~80 kDa, band is represented by TF alone as determined by sequence analysis.

Example 3

Development and Treatment of Tumor Models

The B16 mouse melanoma tumors were developed in first generation hybrid BDF1 (C57 B1 female×DBA/2 male) adult female mice kept at specified pathogen free (SPF) hygienic level. These mice have the complete immune system. The human H-168 melanoma tumors were developed in the homozygous line of C.B.-171 cr scid/scid mice (with severely compromised immune deficiency) which is an inbred mutant strain. In each case, tumor tissue fragments of about 0.1-cm$^3$ were surgically implanted subcutaneously into the intrascapular region to develop the tumors. Each tumor fragment contained 1-1.5×10$^6$ cells. The animals were kept in macrolon cages on ventilated rack at 22-24° C. (50-60% humidity) with lighting regimen of 12/12 h light/dark. The animals had free access to tap water and were fed with sterilized standard diet (Charles River VRF1, Germany) ad libitum. The animals were taken care of according to the "Guiding Principle for the care and use of Animals" based upon the Helsinki declaration and they were approved by the local ethical committee.

The mice bearing the rapidly growing B16 melanoma tumors were used after 8-11 days of tumor transplantation, while mice bearing the slower growing H-168 melanoma were used after 17 days of transplantation. In either case, when the tumor-bearing mice were used, the size of the tumors was in the 0.3-0.6 cm$^3$ range; animals were selected so that in the same treatment group the difference in tumor size was no greater than 0.1 cm$^3$ PALP, TF, or AT were used topically in a cream alone or in combination; in each case, 150-mg cream was applied on the tumor and the vicinity of tumor area (with about 0.3-0.5 cm margin). The tumor volume was determined by using calipers; this technique is well known to one having ordinary skill in the art. Tumor volume was calculated according to the generally accepted formula: V=a$^2$×b×π/6, where "a" and "b" mean the shortest and longest diameter, respectively, of the measured tumor.

Example 4

PALP Preparations Inhibit the Growth of B16 Melanoma

The aggressive B16 mouse melanoma model was developed as described under Example 3. On day 11 after transplantation of tumor cells, the animals were either remained untreated (Group 1) or were treated with 15 mg/kg highly purified PALP via subcutaneous administration (Group 2). In Group 3, the tumors were treated locally with 150-mg of cream containing 4 mg commercial PALP in 1 g of *Vaselinum cholesteratum*. In Group 4, the animals were treated simultaneously locally with commercial PALP containing cream and via subcutaneous injection with highly purified PALP. Each treatment was performed once daily for seven consecutive days (i.e., treatments were terminated on day 18). Each group included 7 animals; the mean values±std. dev. for tumor volumes are shown in TABLE 1. Locally administered PALP preparation, and to a somewhat smaller extent injected purified PALP, inhibited the growth of B16 melanoma. The inhibitory effects remained significant even on day 23, 5 days after the last treatment. When PALP preparations were simultaneously administered via both routes, the combined effects were greater than the individual effects. These results indicate that PALP, particularly in combination with other therapies, can be used to control the growth of this aggressive form of melanoma. While this experiment demonstrated that systemic application of purified PALP is effective against melanoma, the inhibitory effect of locally applied PALP preparation could be caused by either PALP alone or by contaminating TF and/or AT. Alternatively, optimal effects could require the presence of all 3 proteins. Experiments presented later confirm that the inhibitory effects of purified PALP on melanoma growth are greater in the simultaneous presence of TF and AT.

TABLE 1

PALP preparations inhibit the growth of B16 melanoma.

| | Tumor volumes (cm$^3$); days after tumor transplantation | | | | | |
|---|---|---|---|---|---|---|
| Compounds | Day 11 | Day 14 | Day 16 | Day 18 | Day 21 | Day 23 |
| Untreated control | 0.87 ±0.20 | 1.44 ±0.24 | 2.19 ±0.45 | 3.03 ±0.36 | 4.63 ±0.76 | 5.91 ±1.86 |
| PALP, subcutaneous | 0.75 ±0.27 | 1.16 ±0.36 | 1.55 ±0.42 | 2.13 ±0.50 | 3.47 ±0.67 | 3.63 ±0.80 |
| PALP, local | 0.71 ±0.32 | 0.97 ±0.41 | 1.22 ±0.51 | 1.46 ±0.48 | 2.78 ±0.54 | 3.59 ±1.31 |
| PALP, local subcutaneous | 0.79 ±0.28 | 0.81 ±0.37 | 1.00 ±0.35 | 1.35 ±0.42 | 2.08 ±0.45 | 2.87 ±0.46 |
| TF subcutaneous | 0.71 ±0.25 | 1.00 ±0.27 | 1.13 ±0.34 | 2.00 ±0.41 | 3.12 ±0.67 | 3.88 ±0.59 |

Example 5

Effects of Topical Combined Treatments of B16 Melanoma with PALP, TF and AT

Commercial PALP is composed of about 10% PALP, 12% TF, 30% AT, and 35% albumin; the rest (~13%) is composed of mostly derivatives of TF. The major goal in this experiment was to evaluate the effects of individual and combined effects of purified PALP, TF and AT proteins and their combinations on the growth of B16 melanoma at concentrations proportional to their amounts in the commercial PALP preparation.

The B16 mouse melanoma model was developed as described under Example 3. On day 8 after transplantation of tumor cells, the animals either remained untreated (Group 1) or in other animal groups the tumors were treated locally with creams (150 mg per application) containing active components as follows: Group 2, 0.4 mg of purified PALP per 1-g Vaseline; Group 3, 0.5 mg of purified partially iron-saturated TF per 1-g Vaseline; Group 4, 0.4 mg of PALP+0.5 mg TF per 1-g Vaseline; Group 5, 1.2 mg of purified AT per 1-g Vaseline; Group 6, 0.4 mg of PALP+0.5 mg TF+1.2 mg of purified AT per 1-g Vaseline; and Group 7, *Vaselinum cholesteratum* alone. Each treatment was performed once daily on days 8, 11, 13, 15, 18 and 20. Each group included 5 animals; the mean values±std. dev. for tumor volumes are shown in TABLE 2.

The results indicate that while PALP alone had inhibitory effects on melanoma growth, the largest effects were produced by the PALP+TF+AT combination. It seems also clear that PALP+TF combination is more effective than these individual proteins alone. Overall the results confirm that at the concentrations used, the 3 proteins in combination can account for the inhibitory effects of commercial PALP on the growth of B16 melanoma.

Data in TABLE 1 and TABLE 2 lead to the important conclusion that a PALP preparation (such as the presently used commercial preparation) prepared by using the steps described by Ghosh and Fishman [Ghosh, N. K. and Fishman, W. H. (1968), "Purification and properties of molecular-weight variants of human placental alkaline phosphatase," Biochem. J. 108, 779-792] and containing at least PALP and preferably PALP, TF and AT, can be used for the local treatment of skin cancer as the active component of anti-skin cancer products.

TABLE 2

Inhibitory effects of locally administered PALP, TF and AT alone and in combinations on the growth of B16 melanoma.

| | Tumor volumes (cm³); days after tumor transplantation | | | | | |
|---|---|---|---|---|---|---|
| Compound | Day 8 | Day 11 | Day 13 | Day 15 | Day 18 | Day 20 |
| Untreated | 0.41 | 0.94 | 1.79 | 2.81 | 3.90 | 5.16 |
| control | ±0.04 | ±0.16 | ±0.36 | ±0.31 | ±0.70 | ±0.57 |
| PALP | 0.47 | 0.71 | 1.32 | 2.04 | 2.95 | 3.98 |
| | ±0.08 | ±0.17 | ±0.40 | ±0.49 | ±0.68 | ±0.62 |
| TF | 0.34 | 0.79 | 1.38 | 2.19 | 3.07 | 3.83 |
| | ±0.10 | ±0.18 | ±0.14 | ±0.38 | ±0.52 | ±0.50 |
| PALP + TF | 0.44 | 0.69 | 1.06 | 1.41 | 2.29 | 2.67 |
| | ±0.12 | ±0.09 | ±0.28 | ±0.40 | ±0.37 | ±0.58 |
| AT | 0.42 | 0.83 | 1.60 | 2.55 | 3.48 | 4.80 |
| | ±0.11 | ±0.24 | ±0.34 | ±0.48 | ±0.54 | ±0.29 |
| PALP + TF AT | 0.39 | 0.61 | 0.96 | 1.23 | 1.93 | 2.26 |
| | ±0.13 | ±0.10 | ±0.38 | ±0.50 | ±0.42 | ±0.53 |
| Vaseline | 0.45 | 0.98 | 1.70 | 2.98 | 4.08 | 5.28 |
| control | ±0.12 | ±0.14 | ±0.39 | ±0.55 | ±0.30 | ±0.47 |

Example 6

Synthesis of N,N-diethyl-N-methyl-2-[(9-oxo-9H-thioxanthen-2-yl)methoxy]-ethanaminium iodide (Coded as CCDTHT)

This has been performed by using the procedure described in a filed U.S. patent application Ser. No. 11/458,502, filed on Jul. 19, 2006 and entitled "Compounds and compositions to control abnormal cell growth."

Example 7

Combined Effects of CCDTHT and Purified PALP on the Growth of B16 Melanoma

CCDTHT was synthesized as referred to in Example 6. The B16 mouse melanoma model was developed as described under Example 3; in each of the three experimental groups five mice were used. In Group 1, from day 11 (11 days after tumor implantation) until the end of experiment the animals remained untreated. In Group 2, animals received 4.6 mg/kg CCDTHT once daily from day 11 until day 22. In Group 3, animals received 4.6 mg/kg CCDTHT once daily from day 11 until day 22 plus 14 mg/kg highly purified PALP on days 11, 13, 15, 17 and 21. Both CCDTHT and PALP were administered by subcutaneous injection. The mean values±std. dev. for tumor volumes are shown in TABLE 3.

The results show a clear trend that co-administration of purified PALP with a chemotherapeutic agent results in enhanced anti-cancer effect of the latter. Based on the data presented so far, it is reasonable to assume that local administration of PALP particularly in the presence of TF, and AT will also enhance the effects of chemotherapeutic agents.

TABLE 3

Highly purified PALP enhances the effects of CCDTHT on the growth of B16 melanoma.

| | Tumor volumes (cm³); days after tumor transplantation | | | | | |
|---|---|---|---|---|---|---|
| Compounds | Day 11 | Day 14 | Day 16 | Day 18 | Day 21 | Day 23 |
| Control | 0.76 | 1.25 | 1.93 | 2.80 | 4.10 | 5.60 |
| (untreated) | ±0.27 | ±0.23 | ±0.36 | ±0.32 | ±0.57 | ±0.83 |
| CCDTHT | 0.83 | 1.20 | 1.40 | 1.90 | 2.60 | 3.00 |
| | ±0.21 | ±0.37 | ±0.35 | ±0.49 | ±0.47 | ±0.63 |
| CCDTHT + | 0.70 | 0.89 | 1.05 | 1.80 | 2.01 | 2.39 |
| PALP | ±0.30 | ±0.25 | ±0.37 | ±0.40 | ±0.53 | ±0.50 |

Example 8

Effects of Commercial PALP and Chemotherapy on Tumor Growth in Human Melanoma Bearing Mice The H-168 human melanoma model was developed as described in Example 3. When treatments were applied, they always started on day 17 following tumor transplantation. In each experimental group 5 animals were included. Animals in Group 1 remained untreated over the whole experimental period. Animals in the second group were treated with 4.5 mg/kg CCDTHT+0.25 mg/kg of pyrrolidinedithiocarbamate+0.12 mg/kg of zinc chloride 3×5 days for 3 weeks (with 2 days rest after each 5-day period) followed by treatments with only 4.5 mg/kg of CCDTHT for 2×5 days (again with 2 days rest after each 5-day period). For simplicity, in TABLE 4 where the results are presented, this complex treatment is named "chemotherapy". Animals in the third group were treated with 1.5 mg of commercial PALP 5×5 days for 5 weeks (with 2 days rest after each 5-day period). Animals in the fourth group were treated with 4.5 mg/kg CCDTHT+0.25 mg/kg of pyrrolidinedithiocarbamate+0.12 mg/kg of zinc chloride+1.5 mg of commercial PALP 3×5 days for 3 weeks (with 2 days rest after each 5-day period) followed by treatments with 4.5 mg/kg of CCDTHT+1.5 mg of commercial PALP for 2×5 days (again with 2 days rest after each 5-day period). Again, the complex treatment with agents other than PALP is named "chemotherapy". Previously, the combined anti-cancer effects of pyrrolidinedithiocarbamate and zinc chloride, in the absence of CCDTHT or alkaline phosphatase, were reported [U.S. Pat. No. 6,756,063, titled "Methods and compositions for the treatment of human and animal cancers"].

The mean values±std. dev. for tumor volumes are shown in TABLE 4. In the control group (none), only one animal lived on day 55 and day 64. Chemotherapy has not significantly changed survival, while more animals lived on day 64 in the groups treated with PALP alone (3 animals) and the combination of chemotherapy and PALP (3 animals). The combined treatment caused even more dramatic effect on the tumor volume. While chemotherapy alone did not reverse, only slowed down, tumor growth, combination therapy in the 2 remaining animals resulted in the reduction of tumor volume to non-detectable levels (in a 3rd animal the tumor volume was 2.1 cm³ resulting in an average tumor volume of 0.7 cm³). While the exact mechanism of commercial PALP effect remains unknown, long-term treatment of human melanoma with this preparation, and by extension with purified PALP alone or in combination with TF and AT, is likely to enhance the effect of chemotherapy on the reversal of melanoma growth.

It should be noted that in this experiment, injected commercial PALP alone was less effective compared to its effects on B16 melanoma when applied locally. One difference may be that local application is more effective. The other difference may be that in the immune deficient animals, used in this experiment, PALP is less effective because its maximum effect may require intact immune system. For this reason, the B16 melanoma model may prove to be a better system to anticipate the potential effects of PALP and the other proteins on the growth of human melanoma in real patients.

TABLE 4

Injected commercial PALP increases the effect of chemotherapy on tumor weight in H-168 human melanoma bearing mice.

| Treatment | Tumor volumes ($cm^3$); days after tumor transplantation | | | | | | | |
|---|---|---|---|---|---|---|---|---|
| | 17 | 21 | 26 | 31 | 39 | 43 | 55 | 64 |
| None | 0.32 ±0.24 | 1.0 ±0.60 | 1.70 ±1.06 | 2.25 ±0.61 | 3.0 ±0.75 | 4.2(3) ±0.88 | 6.1(1) — | 7.7(1) — |
| Chemotherapy | 0.31 ±0.12 | 0.8 ±0.40 | 1.05 ±0.52 | 1.35 ±0.78 | 1.6 ±0.75 | 2.1(3) ±0.88 | 2.4(2) ±0.93 | 2.7(1) — |
| PALP | 0.29 ±0.08 | 0.9 ±0.30 | 1.35 ±0.27 | 1.8 ±0.56 | 2.4 ±0.79 | 3.3(4) ±0.57 | 4.7(4) ±0.31 | 5.4(3) ±0.54 |
| Chemotherapy + PALP | 0.23 ±0.10 | 0.5 ±0.40 | 1.05 ±0.62 | 1.35 ±0.71 | 1.65 ±0.83 | 2.3(5) ±2.30 | 3.2(4) ±1.12 | 0.7(3) ±0.24 |

Example 9

Effects of Commercial PALP on the Tissue Infiltration of Lymphocytes and Formation of Blood Vessels in B16 Melanoma In the experiment described under Example 7 (data presented in Table 3), additional B16 melanoma bearing animals were treated with *Vaselinum cholesteratum* alone (Vehicle) or with *Vaselinum cholesteratum* containing commercial PALP (PALP) to examine lymphocyte infiltration, formation of blood vessels, and cytokine expression. Tumor tissue samples were taken 4 hours after the 2nd, 4th and 6th treatments.

The excised tumor samples were fixed in 4% paraformaldehyde in phosphate-buffered saline and embedded in paraffin so that several consecutive cross-sections could be made. Sections (5-6 μm) were stained with hematoxylin/eosin ("H&E") with a standard procedure well known in the art. Nine sections derived from 3 animals were evaluated for each treatment for estimating lymphocyte infiltration and blood vessel formation. The size of lymphocytes is about double the size of melanoma cells and the two cell types can be easily distinguished. Blood-containing blood vessels are stained red, which ensures their straightforward recognition. After each treatment with commercial PALP, infiltration of lymphocytes into tumors increased 1.6-2.4-times compared to the same size of untreated tumor samples (data are not shown separately). This suggests that the immune cells and their products (cytokines, other factors) may indeed contribute to the tumor suppressor effects of PALP.

After the 6th treatment with PALP, tumor samples also contained about 2.8-times more red-stained blood vessels per $mm^2$ than untreated tumor samples (data are not shown separately). In view of the ability of PALP to enhance the effect of chemotherapy both in the B-16 and H-168 melanoma models, it is reasonable to assume that PALP acted by enhancing the number of blood vessels in the tumor thereby facilitating distribution of chemotherapeutic agents in the tumor tissue. In turn, increased distribution of chemotherapeutic agents in the tumor tissue will proportionally enhance their anti-tumor effects. Since stimulation of blood vessel formation is likely to take a relatively long time period, this may explain why the effect of PALP and chemotherapy in combination was particularly strong only after about 40 days of starting the treatment.

Example 10

Comparison of the Effects of Injected Commercial PALP, Purified PALP and Transferrin as Well as Locally Applied Commercial PALP on Lung Metastasis of B16 Melanoma B16 melanoma cells are highly metastatic that are known to preferably form metastatic colonies in the lung. The goal of this experiment was to determine if any of the components present in commercial PALP or the mode of application affect the metastatic process.

The B16 melanoma model described under Example 3 was used. The treatments of mice bearing the rapidly growing B16 melanoma were started 11 days after tumor transplantation; additional treatments were performed on each day for six consecutive days. In each experimental group seven animals were used. In the first group, animal tumors were treated locally with 200 mg Vaseline (control group). In the second group, animal tumors were locally treated with 200 mg Vaseline cream containing 4 mg commercial PALP per 1-g Vaseline. In the third group, animals were subcutaneously injected commercial PALP (1.5 mg per animal or 60 mg per kg). In the fourth group, animals were treated with commercial PALP both locally and subcutaneously. In the fifth group, animals were subcutaneously injected highly purified PALP (0.35 mg per animal or 14 mg per 1 kg). In the sixth group, animals were subcutaneously injected partially iron-saturated human TF (0.4 mg per animal or 16 mg per 1 kg). In the seventh group, animal tumors were locally treated with 200 mg Vaseline cream containing 1.0 mg human TF per 1 g Vaseline. In the last group, the tumors were untreated during the entire period of experiment. The macroscopic colonies were counted in the lung (7 animals in each group) 21 days after starting the treatments. The data are presented in TABLE 5; numbers in the parentheses indicate the smallest and highest numbers of metastatic lung colonies in the same group. The results show that subcutaneous administration of TF leads to the doubling of lung metastatic colonies, while other treatments have practically no effects on the metastatic process.

TABLE 5

Subcutaneously administered transferrin increases the
number of metastatic lung colonies of B16 melanoma.

| Treatment | Number of lung colonies per lung* |
|---|---|
| Control (treated locally with Vaseline) | 21 (14-27) |
| Commercial PALP; local applications | 22 (18-27) |
| Commercial PALP; subcutaneo applications | 23 (17-28) |
| Commercial PALP; local + subcutaneo applications | 19 (15-23) |
| Purified PALP, subcutaneous applications | 16 (9-18) |
| TF, subcutaneous applications | 38 (29-44) |
| TF, local applications | 17 (10-21) |
| Control (untreated) | 19 (11-25) |

The invention claimed is:

1. A method for inhibiting growth of an existing skin tumor in a mammal, the method comprising the step of administering to the mammal a composition comprising a therapeutically effective amount of placental alkaline phosphatase and a suitable physiologically compatible carrier to inhibit growth of the existing skin tumor in the mammal.

2. The method of claim 1, wherein the composition is in the form of a cream, a gel, a lotion, an unguent, an emollient, a colloidal dispersion, a suspension, an emulsion, an oil, a spray, a foam, or a mousse.

3. The method of claim 1, wherein the composition is administered topically and the composition comprises 0.01 to 6.0 wt.-% of alkaline phosphatase.

4. The method of claim 1, wherein the step of administering comprises injecting the composition into the skin.

5. The method of claim 4, wherein the total amount of alkaline phosphatase is 0.02 gram to 2.5 gram per square meter of calculated surface area for the mammal.

6. The method of claim 1, wherein the carrier comprises physiological saline solution.

7. The method of claim 1, wherein the step of administering comprises injecting the composition by intravenous, intraarterial, subcutaneous, intramuscular, intracranial or intraperitoneal route.

8. The method of claim 1, wherein the step of administering comprises injecting the composition by intradermal or intratumor route.

9. The method of claim 8, wherein the total amount of alkaline phosphatase is 0.01 mg to 1 mg per injection site.

10. The method of claim 1, wherein the step of administering comprises both a topical and an injection method.

11. The method of claim 10 wherein the administration of topical or injection method is performed simultaneously or sequentially.

12. The method of claim 1 wherein the composition is administered as part of a complex cancer treatment therapy.

13. The method of claim 12 wherein the composition is applied before, during or after the cancer therapy.

14. The method of claim 1 wherein the composition further contains one or more chemotherapeutic agents.

15. The method of claim 14 wherein the chemotherapeutic agent is N,N-diethyl-N-methyl-2-[(9-oxo-9H-thioxanthen-2-yl)methoxy]-ethanaminium iodide, or pyrrolidinedithiocarbamate in combination with zinc.

* * * * *